United States Patent [19]
Dennis

[11] Patent Number: 5,290,245
[45] Date of Patent: Mar. 1, 1994

[54] VALVED CANNULA ASSEMBLY

[75] Inventor: George W. Dennis, Tequesta, Fla.

[73] Assignee: Core Dynamics, Inc., Jacksonville, Fla.

[21] Appl. No.: 870,514

[22] Filed: Apr. 16, 1992

[51] Int. Cl.⁵ .............................................. A61M 5/178
[52] U.S. Cl. .................................... 604/167; 604/169; 604/256; 137/849; 251/149.1
[58] Field of Search ............................... 604/167–169, 604/247–249, 905; 137/843, 845, 849; 251/149.1

[56] References Cited

U.S. PATENT DOCUMENTS

| | | | |
|---|---|---|---|
| 4,245,635 | 1/1981 | Kontos | 604/169 |
| 4,261,357 | 4/1981 | Kontos | 604/169 |
| 5,057,084 | 10/1991 | Ensminger et al. | 604/167 |
| 5,084,023 | 1/1992 | Lemieux | 604/167 |
| 5,098,394 | 3/1992 | Luther | 604/169 |
| 5,125,897 | 6/1992 | Quinn et al. | 604/247 |
| 5,154,701 | 10/1992 | Cheer et al. | 604/169 |

Primary Examiner—C. Fred Rosenbaum
Assistant Examiner—Chalin Smith
Attorney, Agent, or Firm—Thomas C. Saitta

[57] ABSTRACT

A valved cannula assembly having a gasket retaining collar positioned internally within a gasket receiving member, the gasket retaining collar having a recess to receive and retain in a fixed position an annular gasket, which acts in conjunction with either a flapper valve assembly or an inserted instrument to seal the axial bore of the cannula and prevent escape of fluids or gases. A plugging member forces the retaining collar against the gasket receiving member. The recess of the gasket retaining collar is preferably provided with annular ridges to secure the gasket and a conical shoulder to allow some deflection.

8 Claims, 2 Drawing Sheets

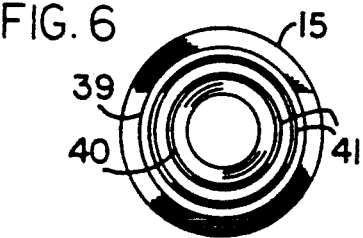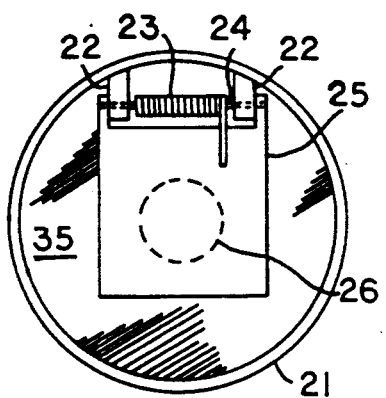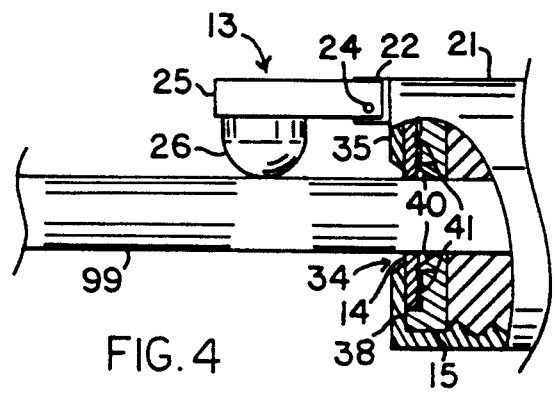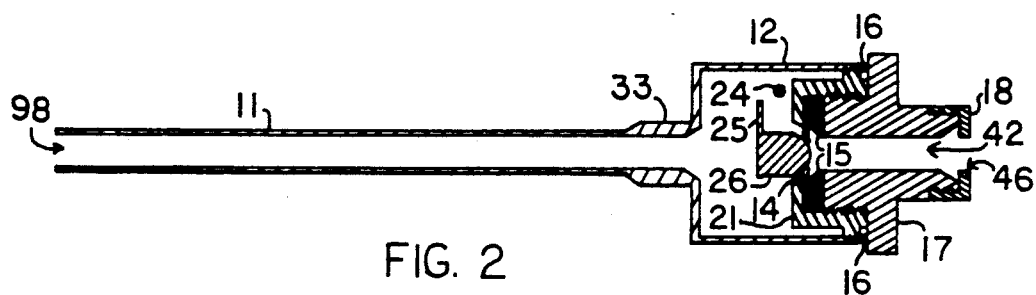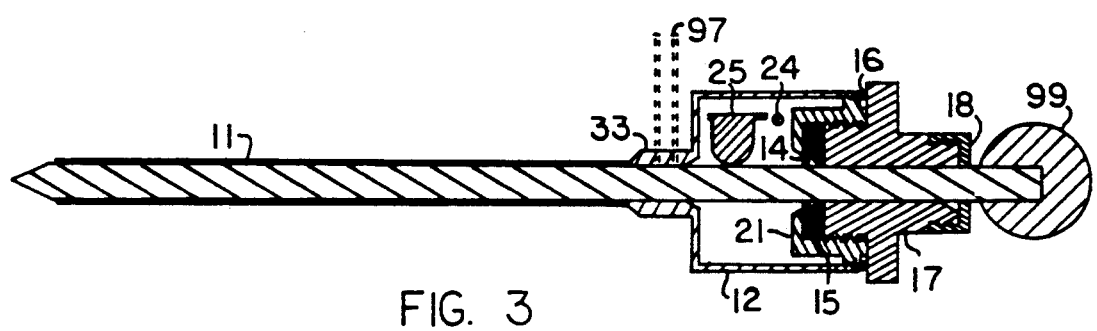

VALVED CANNULA ASSEMBLY

BACKGROUND OF THE INVENTION

The present invention relates generally to the field of cannulas used to provide a conduit and channel through the skin of a patient for performing internal medical procedures. More specifically, the invention relates to such cannulas, both regular and insufflation types, having a valve mechanism to seal off the conduit to prevent fluids or gases from escaping out the exterior end of the cannula. The valve mechanism is of an improved construction and assembly, whereby the integrity of the valve seal is maintained over repeated uses and replacement of the sealing gasket within the valve mechanism is a simple procedure.

Cannulas in combination with trocars are well known in the art. The cannula and trocar combination is used to penetrate the skin of a patient so that medical procedures may be performed internally without recourse to a relatively large incision, the trocar creating only a small puncture site. The internal trocar is removed after penetration and the cannula provides the conduit through which instruments may be inserted and manipulated, or if the cannula is of the insufflation type, gases inserted to expand the internal cavity.

Valved cannulas are well known in the art. For example, U.S. Pat. No. 4,943,280 to Lander, U.S. Pat. No. 4,233,982 to Bauer et al., U.S. Pat. No. 4,245,635 to Kontos and U.S. Pat. No. 4,631,051 to Harris all show valved cannulas. The known devices all suffer from various drawbacks and problems which are not present in the cannula of the invention. To provide a gas-tight and fluid-tight seal, a typical valve mechanism comprises a pivoting plug in combination with a resilient gasket, the plug being adapted to be pushed open by the inserted instruments and the gasket forming a seal with either the plug or the inserted instrument. The integrity of the seal depends upon the gasket continuing to perform its function over many repeated usages. The known devices fall into two main categories—those with an exposed gasket, as in Bauer et al., and those with intricately shaped gaskets, as in Lander.

A cannula is typically used with pointed or hooked instruments, and it is important that the sharp portions of the instruments not contact the sealing gasket. Some cannulas have the gasket positioned on the pivoting plug member. This is a poor design, in that it exposes the gasket to contact with the trocar or other instruments every time they are inserted to force open the valve, since the gasket is not stationary about the central axis of the cannula shaft. This often results in slicing or tearing of the gasket. Using a fixed gasket alleviates this problem, but the current assemblies require complicated gaskets which can wear out from fatigue or have large exposed surfaces allowing shifting or stretching of the gasket.

The valve mechanism of the invention solves these problems by providing a simple annular gasket which is maintained in a fixed position relative to the central a is. The retaining means for the gasket provide for an improved seal with the valve plug and allow for easy removal and replacement of the gasket when necessary.

SUMMARY OF THE INVENTION

The invention is an improved cannula assembly having a flapper valve to seal the insertion channel for the trocar or other instrument when the trocar or other instrument is removed from the cannula. A cannula and trocar combination is used to create a conduit through the skin of a patient into an internal area where medical procedures need to be performed. The trocar is the piercing implement and is removed from the cannula assembly once the insertion has been made. The cannula then provides a conduit through which instruments can be inserted for observation or surgical procedures, or in the case of insufflation cannulas, gases for internal inflation of the proximate area within the patient. It is necessary to provide means to seal off the cannula conduit to prevent loss of fluids or gases, both when instruments are inserted as well as when no instruments are in place within the cannula.

The improvement comprises the provision of a gasket retaining collar positioned internally within a gasket receiving member which together act to maintain a flexible annular gasket in proper position to act as the seat for the round valve plug of the flapper valve attached to the gasket receiving member, to seal off the conduit when no instruments are inserted, and as a seal surrounding inserted instruments when procedures are being performed. The gasket remains stationary during instrument insertion and removal, and is not susceptible to damage from cutting or piercing instruments which can cause failure in the gasket's sealing properties. The gasket retaining collar has a conical central aperture to provide optimum seating of the circular in cross-section valve plug and annular rims to fix and improve the sealing characteristics of the gasket. A plugging member which threads into the gasket receiving member forces the gasket retaining collar and gasket tightly against the inside of the gasket receiving member to maintain the gasket securely in position, while allowing for easy removal and replacement of the gasket when necessary.

BRIEF DESCRIPTION OF THE DRAWINGS

FIG. 2 is a longitudinal cross-sectional view of the invention.

FIG. 3 is a cross-sectional view of the invention corresponding to FIG. 2, here shown with a trocar inserted.

FIG. 4 is a partial view of the invention showing the flapper valve assembly and a partially exposed gasket receiving member with the seating gasket, gasket retaining collar and plugging member in place.

FIG. 5 is a view of the distal end of the gasket receiving member showing the flapper valve assembly.

FIG. 6 is a view of the distal end of the gasket retaining collar showing gasket recess containing the conical shoulder and ridges.

DETAILED DESCRIPTION OF THE INVENTION

Figure 1:
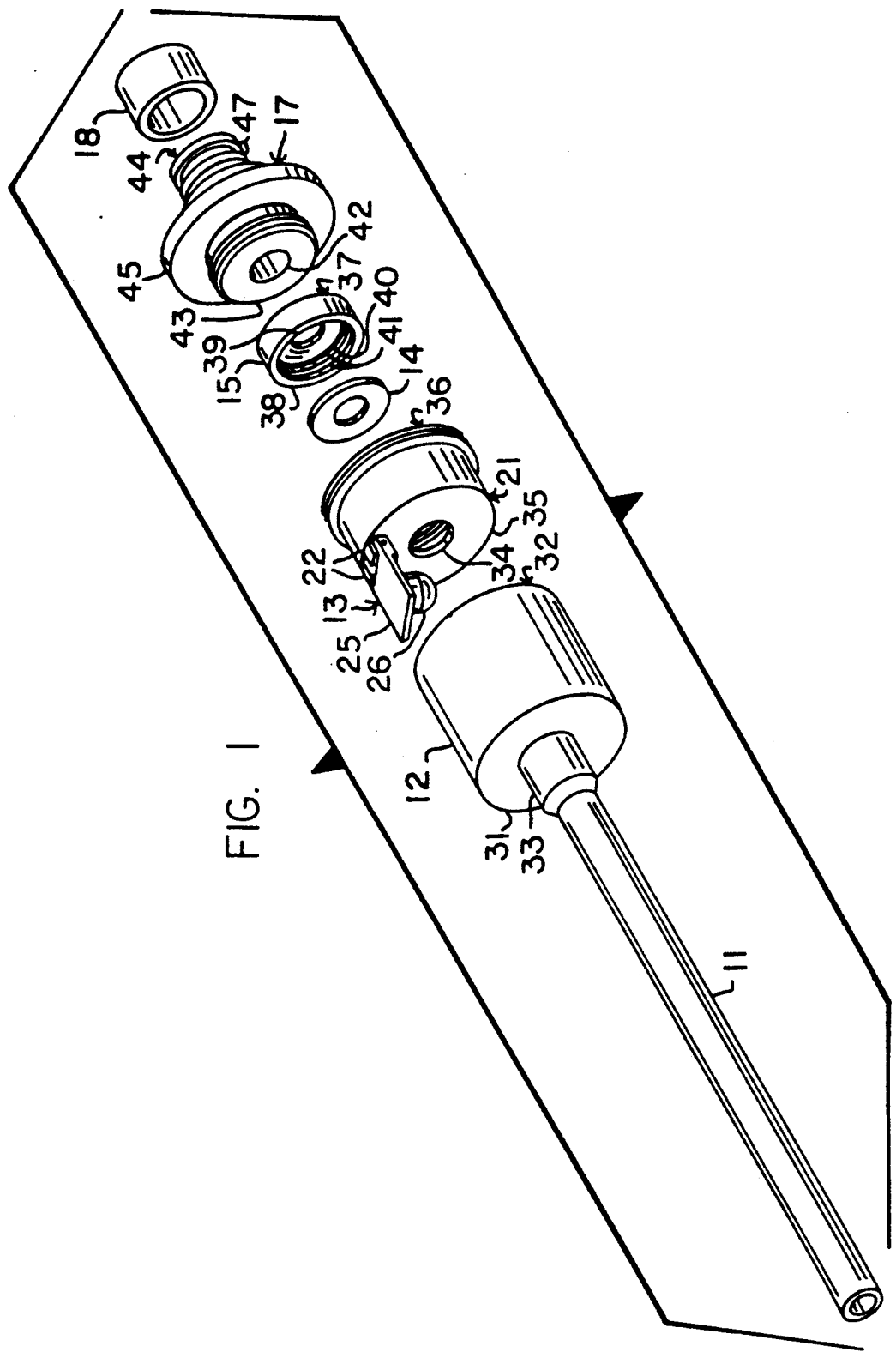
FIG. 1 is an exploded isometric view of the components of the invention.

With reference to the drawings, the best mode and preferred embodiment of the invention will now be set forth in detail. With regard to this description, the term distal shall be used to refer to the direction relative to the far end of the cannula assembly, the end to be inserted in the patient, and the term proximal shall refer to the direction relative to the near or external end of the cannula assembly.

As shown in FIGS. 1 through 3, the cannula assembly comprises in general the combination of a cannula sleeve 11, a valve housing 12, a flapper valve assembly 13, a seating gasket 14, a gasket retaining collar 15, an O-ring 16, a plugging member 17, and an end seal 18, all components being interconnected coaxially to share a common central axis. In this manner the cannula assembly provides a longitudinal central bore 98 for insertion and removal of a trocar 99 or other medical instruments. The flapper valve assembly 13 comprises a gasket receiving member 21, a flapper mounting bracket 22, a spring member 23, a spring post 24, a valve plate 25, and a valve plug 26, connected in such a manner that the valve plate 25 and the valve plug 26 pivot relative to the gasket receiving member 21 to provide an open or closed seal in conjunction with a seating gasket 14.

The valve housing 12 is generally tubular with the distal end 31 closed except for the smaller central bore 98 leading down the cannula sleeve 11, the cannula sleeve 11 being mounted coaxially onto the distal end 31 of valve housing 12 with a preferably thickened reinforcing shoulder 33 to provide greater strength at the juncture. Adjacent the proximal end 32 of valve housing 12, the valve housing 12 is internally threaded a short distance into the interior. Valve housing 12 provides an open internal area to allow for placement and unobstructed movement of the valve flapper assembly 13. The valve housing 12 may also have a gas insufflation port 97, shown by outline in FIG. 2, preferably mounted onto the reinforcing shoulder 33 at the junction of cannula sleeve 11 and valve housing 12. This allows pressurized gas, such as carbon dioxide or the like, to be forced through the central bore 98 of cannula sleeve 11 and into the patient.

As shown in FIGS. 4 and 5, the flapper valve assembly 13 comprises a pivoting valve mechanism which is attached to the gasket receiving member 21. Gasket receiving member 21 is generally tubular in shape with the distal end 35 closed except for a circular valve aperture 34 centered on the central axis of gasket receiving member 21, with this central axis corresponding to the central bore 98 of the cannula assembly. The gasket receiving member 21 is externally threaded adjacent its proximal end 36 to correspond and mate with the internal threading of the valve housing 12, such that the gasket receiving member 21 is contained completely within the interior portion of valve housing 21 when the two components are interconnected. The longitudinal length of gasket receiving member 21 is roughly half the longitudinal length of valve housing 12, such that the distal end 35 of gasket receiving member 21 will be positioned approximately in the middle of valve housing 12, leaving sufficient space for unobstructed movement of the valve plate 25.

Distal end 35 of gasket receiving member 21 is preferably planar, and the flapper valve mechanism is mounted onto this surface. In the embodiment shown, mounting brackets 22 retain spring post 24, upon which is mounted a spring member 23 and a valve plate 25 containing the valve plug 26. Spring member 23 is mounted so as to maintain the valve plate 25 disposed relatively parallel to the distal end 35 of gasket receiving member 21, such that valve plug 26 extends into and through the valve aperture 34 when no trocar 99 or other instrument is inserted into the cannula assembly. Spring member 23 allows the valve plug 26 and valve plate 25 to be pivoted away from the central axis by the insertion of trocar 99 or other instrumentation, as shown in FIG. 5. Removal of trocar 99 allows spring member 23 to force valve plate 25 back to the parallel closed position. It is preferred that valve plate 25 be mounted onto spring post 24 with a small tolerance for movement in the axial and radial directions of the spring post 24. This allows for small movement of valve plate 25 and valve plug 26 in all directions, thus assuring optimal seating with seating gasket 14. Valve plate 25 and valve plug 26 are preferably composed of stainless steel or like material, such that the points and hooks of the trocar 99 or other instrument will not cut or damage the surface of valve plug 26. Valve plug 26 is preferably shaped to have a circular cross-section at the mating region for optimum contact with the seating gasket 14 and to minimize contact with the trocar 99 or other instruments inserted and removed from the cannula assembly. Such a cross-section may be obtained by providing valve plug 26 with an end of a spherical, conical, elliptical, or the like, configuration.

Seating gasket 14 is an annular member with a thin cross-section and having a central opening sized slightly smaller than that of central bore 98. Seating gasket 14 may be comprised of any suitable gasket material known in the art capable of forming a complete seal in conjunction with valve plug 26. Preferably, seating gasket 14 is flexible and slightly elastic to optimize the seal between itself and the valve plug 26 or the trocar 99 or other instrument inserted in the device. Seating gasket 14 is maintained in the coaxial position flush against the internal side of the distal end 35 of gasket receiving member 21 by gasket retaining collar 15. Gasket retaining collar 15 is an annular member having a relatively planar proximal side 37 and an outer diameter slightly smaller than the internal diameter of gasket receiving member 21. The distal side 38 is planar to mate flush with the interior of the distal end 35 of gasket receiving member 21 and has a gasket recess 39 to contain the seating gasket 15, as shown in FIG. 6. Gasket recess 39 is preferably structured to have a conical shoulder 40 surrounding the central opening and annular sealing ridges 41 concentric to the central opening. The sealing ridges 41 press into the seating gasket 14 and create a better seal, while the conical shoulder 40 is directed toward the valve plug 26. This allows the seating gasket 14 to deflect a small amount under the pressure of the valve plug 26 to create a better seal, while at the same time preventing extreme distortion of the seating gasket 14 by the valve plug 26. The gasket retaining collar 15 presses the seating gasket directly against the interior wall of the distal end 35 of gasket receiving member 21, maintaining it in the proper position during repeated uses of the cannula assembly and preventing excess distortion of seating gasket 14 during insertion and removal of trocar 99 or other instruments.

Gasket receiving member 21 is internally threaded over substantially its entire length to receive and interconnect with plugging member 17. Plugging member 17 is a relatively solid body having an axial bore 42 extending completely through. The distal portion 43 of plugging member 17 is externally threaded and sized to mate coaxially with the internally threaded gasket receiving member 21. An annular gripping shoulder 45 having an outer diameter greater than the outer diameter valve housing 12 is positioned on the plugging member 17 whereby the distal side of the gripping shoulder 45 is adjacent the proximal end 32 of valve housing 12 when the plugging member 17 is fully threaded into the gasket receiving member 21. The distal end 43 of plugging member 17 is planar and abuts the proximal side 37 of gasket retaining collar 15 when the plugging member 17 is fully threaded into the gasket receiving member 17, thus securing the gasket retaining collar 15 and the seating gasket 14 tightly against the gasket receiving member 21. An O-ring 16 of suitable size and material is disposed between the griping shoulder 45 of plugging member 17 and the proximal end 32 of valve housing 12 to completely seal the combination at the junction. Gripping shoulder 45 is preferably scored or ridged to facilitate joining and disjoining the plugging member 17 from the valve housing 12. The proximal end 44 of plugging member 17 is structured to provide an end seal retaining member 47 to retain a flexible end seal 18. End seal retaining member 47 is preferably a series of annular ridges as shown in the figures, with end seal 18 having a corresponding internal shape. End seal 18 has an instrument opening 46 sized to sealingly grip the shaft of any trocar 99 or instrument inserted into the cannula assembly. End seal 18 is formed of any suitable flexible and elastic material. End seal 18 provides a secondary seal, in combination with the primary seating gasket 14, to prevent escape of gases or fluids from the cannula assembly when a trocar 99 or instrument is in place in the device. The proximal end of axial bore 42 may be flared to allow for easier insertion of the trocar 99 or instrument into the cannula assembly.

To use the cannula assembly for puncturing the patient's skin, the trocar 99 is inserted through the end seal 18, the axial bore 42 of plugging member 17, and the seating gasket 14. The point of the trocar 99 pushes against valve plug 26, thus pivoting it and valve plate 25 away from the central axis, as shown in FIG. 3. The trocar can then be extended completely through the central bore 98 of cannula shaft 11 and the point exposed. After puncture, the trocar 99 is removed from the cannula assembly, with spring member 23 closing valve plate 25 and seating valve plug 26 into seating gasket 14, thus sealing off the internal opening into the patient. If necessary, gas may be forced into the body cavity through insufflation port 97, the combination of valve plug 26 and seating gasket 14 preventing escape of the gas through the axial bore 42 of plugging member 17. Insufflation port 97 is preferably a conduit fitting for quick attachment of tubes or valves and simple sterilization and cleaning, but could also incorporate its own valve mechanism if desired. Other instruments can now be inserted into the cannula assembly through end seal 18, plugging member 17, flapper valve assembly 13 and cannula shaft 11, the seating gasket 14 conforming to the instrument shaft and preventing escape of gas or fluid past the instrument.

As the flexibility of the seating gasket 14 deteriorates after repeated uses over time, it will be necessary to replace the seating gasket 14. The construction of the device allows a relatively inexpensive planar annular gasket to be used, and the threaded mechanism of joining the various body components allows easy replacement. Except for the seating gasket 14, the 0-ring 16 and the end seal 18, all components may be constructed of stainless steel, chromed brass, hard plastic or other similar material able to be sterilized and reused.

The illustrations set forth above are by way of example only, and certain substitutions and equivalents for the components described above may be obvious to those skilled in the art. The true definition and full scope of the invention therefore is to be as set forth in the following claims.

I claim:

1. In a valved cannula assembly for use with inserted instruments, the valved cannula assembly including a cannula sleeve, a valve housing having an internal open area, a flapper valve assembly having a plugging member adapted to be moved by said inserted instruments, a seating gasket and an axial bore for insertion and removal of said instruments, where the seating gasket in combination with the plugging member of the flapper valve assembly or an inserted instrument creates a seal in the axial bore, the improvement comprising the combination of:

an annular seating gasket having a relatively thin cross-section and a central opening sized slightly smaller than said axial bore;
   a gasket receiving member positioned within said valve housing, said gasket receiving member having a relatively planar distal end with a central aperture positioned thereon, said gasket receiving member having said flapper valve assembly mounted on said distal end within said internal open area of said valve housing, whereby said plugging member extends through said central aperture to contact said central opening of said seating gasket;
   an annular gasket retaining collar having a recess adapted to receive said seating gasket and retain said seating gasket in fixed position against said distal end of said gasket receiving member whereby said distal end is between said seating gasket and said flapper valve assembly; and
   a plugging member abutting said gasket retaining collar and connected to said gasket receiving member whereby said gasket retaining collar is retained in a fixed position against said distal end of said gasket receiving member.

2. The assembly of claim 1, where said recess of said gasket retaining collar further comprises annular ridges.

3. The assembly of claim 1, where said recess of said gasket retaining collar further comprises a conical shoulder to allow slight deflection of said gasket.

4. The assembly of claim 1, where said gasket receiving member is internally threaded and said plugging member is correspondingly externally threaded to connect with said gasket receiving member.

5. The assembly of claim 1, further comprising an insufflation port for admission of gases to said internal open area of said valve housing and said cannula sleeve.

6. The assembly of claim 1, where said gasket receiving member is externally threaded and said valved housing is correspondingly internally threaded to connect with said gasket receiving member.

7. The assembly of claim 1, further comprising an O-ring abutting said valved housing and said plugging member.

8. The assembly of claim 1, further comprising an end seal mounted onto said plugging member.

* * * * *